(12) United States Patent
Pinkus et al.

(10) Patent No.: US 7,235,779 B1
(45) Date of Patent: Jun. 26, 2007

(54) NIGHT VISION-WEIGHTED IRRADIANCE TESTING

(75) Inventors: Alan R. Pinkus, Bellbrook, OH (US); Harry L. Task, Dayton, OH (US); Sheldon E. Unger, Englewood, OH (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 204 days.

(21) Appl. No.: 10/975,128

(22) Filed: Oct. 20, 2004

(51) Int. Cl.
*G01D 18/00* (2006.01)
(52) U.S. Cl. .................................................. 250/252.1
(58) Field of Classification Search .............. 250/252.1
See application file for complete search history.

(56) References Cited

U.S. PATENT DOCUMENTS

| | | | |
|---|---|---|---|
| 3,730,985 A | | 5/1973 | Whitney |
| 3,930,149 A | * | 12/1975 | French ........................ 362/285 |
| 4,309,608 A | | 1/1982 | Adamson, Jr. et al. |
| 4,328,516 A | | 5/1982 | Colpack et al. |
| 4,415,921 A | * | 11/1983 | Mulvanny et al. .......... 348/191 |
| 4,607,923 A | | 8/1986 | Task et al. |
| 5,070,239 A | | 12/1991 | Pinkus |
| 5,169,234 A | | 12/1992 | Böhm |
| 5,567,937 A | | 10/1996 | Pinkus |
| 5,679,949 A | | 10/1997 | Task et al. |
| 5,717,608 A | | 2/1998 | Jensen |
| 6,194,701 B1 | | 2/2001 | Task et al. |
| 6,196,845 B1 | | 3/2001 | Streid |
| 6,414,305 B1 | | 7/2002 | Bendall |

OTHER PUBLICATIONS

Task, Night vision goggle visual acuity assessment: results of an interagency test, Proceedings of the SPIE, vol. 4361 (Aug. 2001), pp. 130-137.*
P. Marasco et al., "The Impact of Target Luminance and Radiance on Night-Vision Device Visual Performance Testing," Proceedings of SPIE, 2003, pp. 174-183, vol. 5079.
Hoffman Engineering Corp., "*Model ANV-120, System Gain Test Set for Gen-II and Gen-III Night Vision Devices*," Jul. 24, 1998, pp. 1-25.

* cited by examiner

*Primary Examiner*—David Porta
*Assistant Examiner*—Shun Lee
(74) *Attorney, Agent, or Firm*—AFMCLO/JAZ; Gerald Hollins

(57) ABSTRACT

A self-contained, military usage compatible, stabilized illumination calibration system and method of using same to enable in-the-field accurate determination of the low-level light falling on the surface of a night vision apparatus resolution chart and attending adjustment of a night vision device. Use of such charts, such as the chart of U.S. Pat. No. 4,607,923, preferably includes known levels of illumination at several different expected night vision goggle compatible lower-levels in order to both evaluate and adjust the performance of a night vision device prior to its use or during extended use periods. The disclosed system is digital computer controlled and provides an accurate, easy to use, and low cost alternative to previous laboratory-like methods of determining night vision evaluation illumination. The disclosed system provides go or no go indications of achieved chart illumination.

24 Claims, 10 Drawing Sheets

Discrete Level NVIS-Weighted Irradiance Tester

NIGHT VISION-WEIGHTED IRRADIANCE TESTING

RIGHTS OF THE GOVERNMENT

The invention described herein may be manufactured and used by or for the Government of the United States for all governmental purposes without the payment of any royalty.

COMPACT DISC APPENDIX

The present document includes a single compact disc appendix, submitted in two identical disc copies identified as "Copy 1" and "Copy 2", each containing only the 16 kilobyte file identified as "GNG-PO.txt". This file provides a program listing for software used in operating the apparatus of the present invention and is referred-to in the application specification. This GNG-PO file is listed in ASKII code as is accomplished with the "plain text" option of a "Windows 2003 XP" operating system. The disclosed computer code is in the format of the Parallax Inc. Stamp BASIC Interpreter programming language. This file may also contain a reference to the present invention using one or more of the names GNG tester, Go No-Go tester and Discrete-Level NVIS-Weighted Irradiance Tester. A transmittal letter provides supplemental information regarding the "Copy 1" and "Copy 2" discs. The content of the GNG-PO compact disc file is hereby incorporated by reference herein. The GNG-PO file was created on May 15, 2003 and bears a May 19, 2005 present disc creation date.

BACKGROUND OF THE INVENTION

Currently, United States military personnel use the U.S. Air Force Resolution Chart of U.S. Pat. No. 4,607,923 issued to Task et al. in 1986 when evaluating or adjusting night vision goggle devices. This resolution chart is now a standard for use by U.S. and allied military units performing night vision goggle missions. This chart has a series of increasingly finer pairs of black and white bars, bars that, when viewed through night vision goggles, allow maintenance personnel to evaluate and adjust the image quality and allow the war fighter to personally perform night vision adjustments such as objective lens focusing, interpupillary distance selection, tilt angle adjustment, eyepiece selection and battery checking prior to a night vision mission. For language convenience purposes the several functions accomplished with aid of the present invention may be referred-to as "tuning" of a night vision device.

Proper use of this resolution chart however requires it to be precisely irradiated at several different levels, levels corresponding to no moon presence, quarter moon presence, half moon presence and full moon presence during usage. This chart usage irradiance is also preferably accomplished with the aid of an irradiance-measuring instrument such as a photometer or a radiometer or less preferably with human estimation of irradiance level. Photometer and radiometer instruments range in value from $5,000 to $28,000 or greater as may be observed in the catalog or on the web site of one supplier of such instruments, Hoffman Engineering Corporation of Stamford, Conn., http://www.hoffmanengineering-.com. Such instruments are also generally unsuited for use under military field conditions as is dictated by their cost and their substantially fragile nature.

The present invention is believed to provide an answer for these difficulties.

The U.S. Pat. No. 4,607,923 and each other patent document and reference document identified herein are also hereby incorporated by reference herein.

SUMMARY OF THE INVENTION

The present invention provides in the field achievement of "standardized" irradiance for evaluation and adjustment of night vision systems.

It is an object of the invention to measure night vision related irradiance levels accurately and economically.

It is an object of the invention to provide a test irradiance measuring system for the irradiance levels used with night vision apparatus under military field conditions.

It is an object of the invention to provide a test irradiance measuring system for the plurality of irradiance levels used with military night vision apparatus.

It is an object of the invention to provide a portable night vision irradiance measuring system adapted to successful usage by unskilled personnel.

It is an object of the invention to provide a stable, battery-operated, computerized measuring system for night vision compatible low irradiance levels.

It is an object of the invention to provide an irradiance measuring system compatible with an existing night vision apparatus resolution chart.

It is an object of the invention to provide an irradiance measuring system based on the stable characteristics of a photodiode transducer device.

It is an object of the invention to provide an irradiance measuring system that is disposable in a plurality of physical mounting arrangements.

It is an object of the invention to provide an irradiance measuring system producing a simple output indication in response to a plurality of sought after irradiance conditions.

It is an object of the invention to provide an irradiance measuring system providing an easily comprehended digital-like irradiance level output indication.

It is an object of the invention to provide an irradiance measuring system producing an irradiance level output indication that is remotely comprehensible.

It is an object of the invention to provide an irradiance measuring system providing an output indication that is free of night vision device interference generation.

It is an object of the invention to provide an irradiance measuring system capable of both convenient field use and replacement of more costly laboratory equipment.

These and other objects of the invention will become apparent as the description of the representative embodiments proceeds.

These and other objects of the invention are achieved by portable military field use night vision device evaluation apparatus comprising the combination of:

a standardized military night vision device performance assessment chart including a plurality of night vision device resolution patterns of selected line density and line spacing character;

a source of military night vision device compatible selectable irradiance levels disposable in illuminating proximity with said military night vision device performance assessment chart;

a portable irradiance intensity measuring apparatus disposable within an area irradiated by said source of military night vision device compatible selectable irradiance levels including low level irradiance in physical proximity with said military standardized night vision device performance assessment chart;

said portable irradiance intensity measuring apparatus including a received irradiance to first electrical signal transducer element, a plurality of selectably accessed standardized ambient irradiance-related reference second electrical signals and an electrical signal comparison apparatus connecting with each said first and second electrical signals;

said electrical signal comparison apparatus including analog to digital converter and signal processing elements coupled to an evaluation apparatus contained remotely visible graphic multiple luminous element military night vision device-indiscernible irradiance level indicating display.

BRIEF DESCRIPTION OF THE DRAWING

The accompanying drawings incorporated in and forming a part of the specification, illustrate several aspects of the present invention and together with the description serve to explain the principles of the invention. In the drawings:

FIG. 2 includes the views of FIG. 2a, FIG. 2b and FIG. 2c in which:

DETAILED DESCRIPTION OF THE INVENTION

Figure 1:
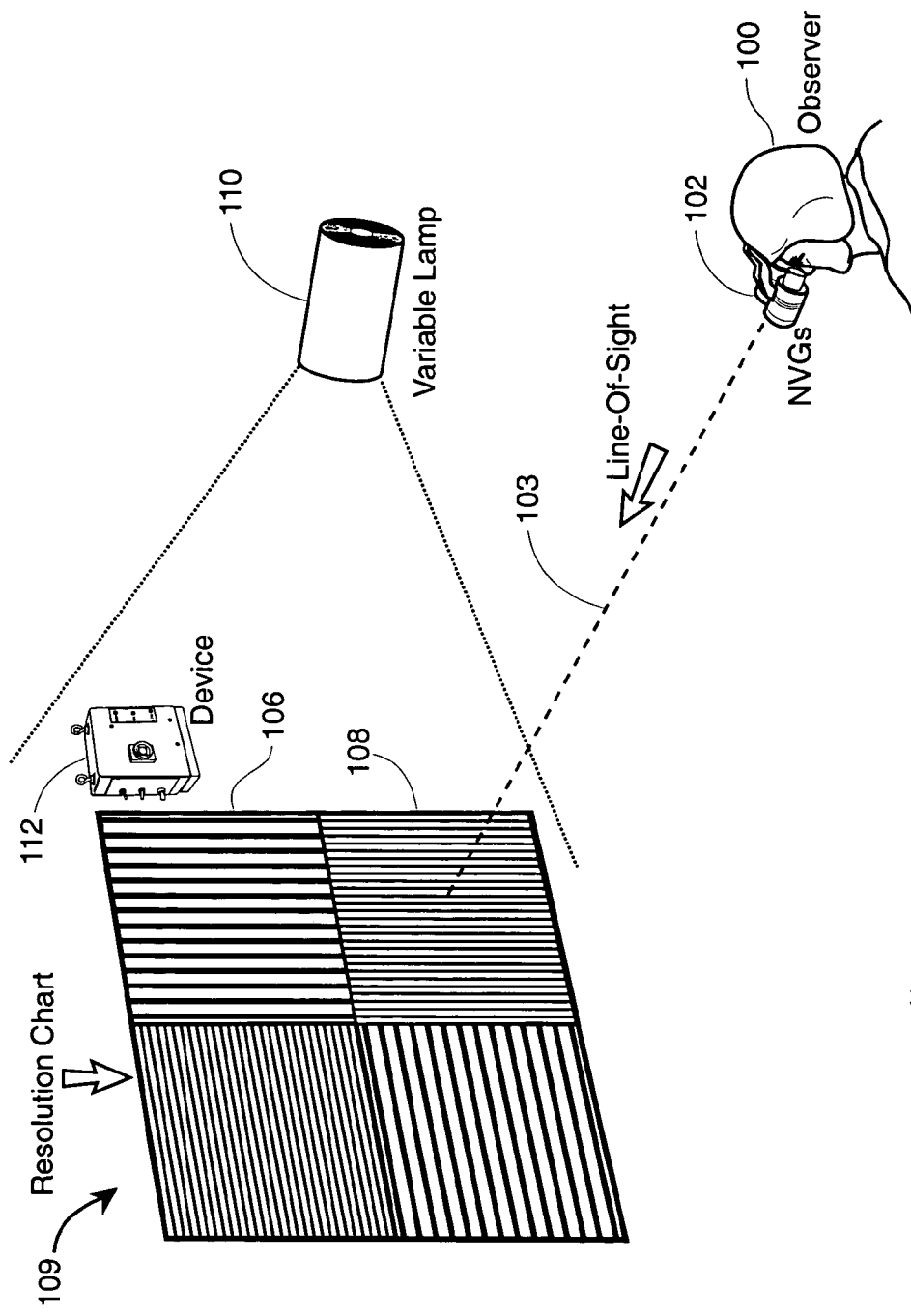
FIG. 1 shows use of a dimly illuminated resolution chart to adjust and evaluate a set of night vision goggles.

FIG. 1 in the drawings illustrates the general method by which U.S. military personnel use the resolution chart of U.S. Pat. No. 4,607,923 to adjust and evaluate a set of night vision goggles or other night vision apparatus. In the FIG. 1 drawing an observer 100 is viewing the resolution chart 104 along the line of sight 103 by way of the night vision goggles 102. The chart 104 is irradiated with a controlled source of irradiance 110 using the aid of a measuring device 112 made in accordance with the present invention to determine the level of night vision goggle sensitive irradiance received on the chart 104. The FIG. 1 resolution chart 104 displays a representative series of electrical square-wave generating patterns (i.e., alternating black and white lines) of low to high spatial frequency (i.e., from coarse to fine line sizes and spacing as are represented at 106 and 108 for example).

The patterns of the FIG. 1 chart 104 allow the observer 100 to make fine changes to the several adjustment controls of the night vision goggles 102. These adjustments may include objective and eyepiece focusing, interpupillary distance adjustment and tilt of the goggles axis with respect to the observer's line-of-sight for examples. After performing these adjustments, the highest observable pattern, the finest of the gratings 106, 108 and so on resolved, is then an indication of the goggle's ability to resolve fine detail. The performed adjustments may achieve as much as a 20/30 Snellen acuity or a 1.5 minutes of arc degree of resolution capability for example. Any goggle performance problems such as less than optimum focusing or loss of resolution are usually discernible during one or more tests performed in the FIG. 1 manner.

As may be understood by the presence of the measuring device 112 in the FIG. 1 scene the measurements accomplished in this scene include resolution determinations accomplished at several different irradiance levels of the chart 104. Notably a night vision goggle or other night vision device tested in the FIG. 1 manner may perform adequately at full moon irradiance level but fail under a lower clear starlight irradiance level for example. Such performance gaps or lapses inevitably adversely affect night vision device usage during a low light level mission.

Typically the FIG. 1 chart 104 is dimly irradiated by variable incandescent lamps comprising the source 110 in the FIG. 1 drawing. The U.S. Army and other users for example employ a standard lamp of 2856 degrees Kelvin color temperature for the irradiation source 110. Such a source of known color temperature is needed for performing the FIG. 1 test because the goggles being adjusted are inherently wavelength sensitive devices, i.e., are expressly arranged to be responsive to a specific band of input wavelengths, such as 665 to 930 nanometers, while largely rejecting wavelengths outside of this band. A shift of input energy toward or away from this band of wavelengths thus has a direct effect on goggle output level.

Figure 2A:
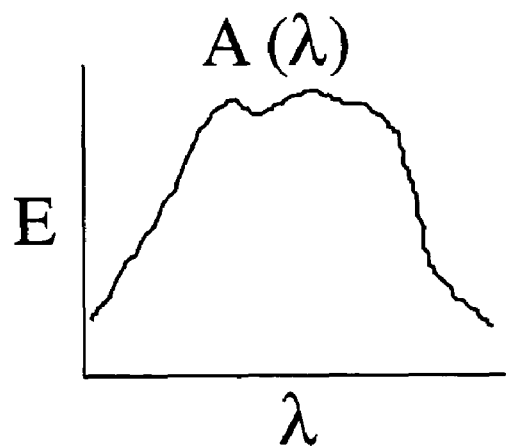
FIG. 2a shows the spectral energy distribution of a typical nighttime ambient irradiation.

During the FIG. 1 chart usage the measuring device 112 provides an indication of the level of night vision goggle-sensitive irradiance received by the chart 104. A series of drawing figures and equations as follows may be used to describe the underlying concepts upon which this irradiance-measuring device 112 operates. FIG. 2a in the drawings for example shows the spectral irradiance distribution $A(\lambda)$, i.e., spectral irradiance plotted as a function of wavelength, for representative ambient nighttime irradiance conditions such as a full moon, quarter moon, clear starlight or overcast starlight condition. Wavelength based plots for other elements of the FIG. 1 apparatus appear in the FIG. 2b and FIG. 2c drawings. In order to better appreciate the present invention and its differences from other light measuring arrangements, such as may be used in the photography or television fields for examples, it is perhaps informative to realize that the light levels under consideration in the FIG. 1 drawing are extremely low and involve wavelengths that are essentially invisible to the unaided human eye.

Figure 2B:
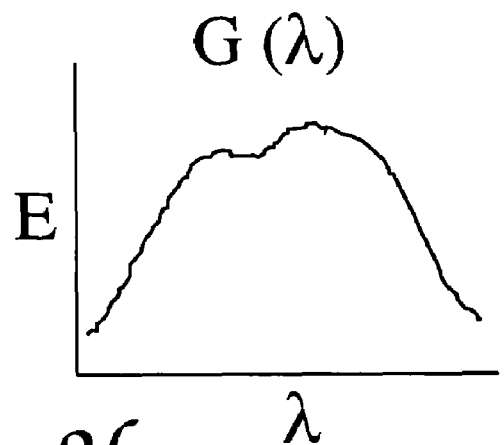
FIG. 2b shows the spectral energy band pass of a typical night vision device.
Figure 2C:
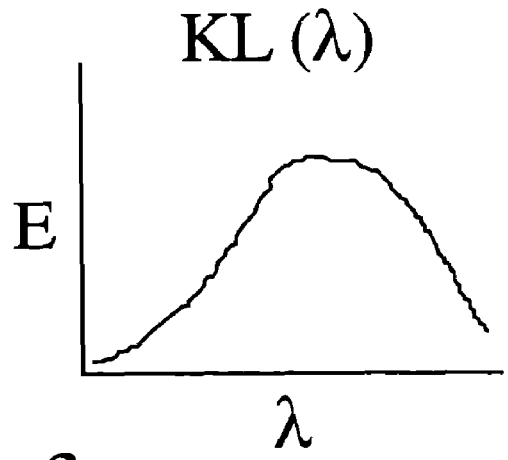
FIG. 2c shows the spectral energy distribution of a typical variable incandescent light source.

FIG. 2b shows the spectral sensitivity $G(\lambda)$ of a given set of night vision goggles, for example Generation III types A, B, or leaky green goggles, also as a function of wavelength. FIG. 2c shows the spectral irradiance distribution of a variable intensity variable color temperature, incandescent light source (L). Equation [1], shown below, uses the FIG. 2b and FIG. 2c data to define the integrated, night vision goggle-weighted irradiance $Q_{AMBIENT}$, for a given goggle and nighttime irradiance. $Q_{AMBIENT}$, is equal to the definite integral with respect to wavelength from 600 to 1000 nanometers of the product of goggle spectral sensitivity and ambient illumination spectral irradiance distribution. Equation [2] defines $Q_{LAMP}$ for a goggle and a given variable intensity (K) incandescent light source (L) used to irradiate the resolution target. $Q_{MMP15}$ is equal to the definite integral with respect to wavelength from 600 to 1000 nanometers of the product of goggle sensitivity and the incandescent lamp spectral energy distribution.

In order for a resolution test condition as represented in FIG. 1 to be equivalent to an actual nighttime condition, i.e., a low-light level condition with a specific spectral distribution, $Q_{LAMP}$ must equal $Q_{AMBIENT}$. (Q is a constant for any given illumination and goggle combination). It follows, that when Equations [1] and [2] are equivalent, equality is achieved by varying the intensity K of the irradiation falling on the resolution chart as is shown by Equation [3]. In Equation [3] an expression of equality of the two integrals is rearranged to define K. Note that in order to vary the intensity of the irradiance falling onto the FIG. 1 chart 104 while still maintaining a preset blackbody temperature of about 2856 K, the light source 110 is moved closer to or farther away from the chart or an illumination controlling device such as the aperture of an iris is changed in diameter. Dimming of a lamp by changing its operating voltage cannot be used for intensity change purposes since this results in a change of lamp operating temperature and spectral distribution.

In the FIG. 2 waveforms and in Equations [1], [2] and [3]

Q=integrated NVG-weighted irradiance $A(\lambda)$=spectral irradiance distribution of a given nighttime ambient condition $G(\lambda)$=spectral sensitivity of a given set of night vision goggles $L(\lambda)$=spectral irradiance distribution of a variable light source (L)

K=irradiance level adjustment constant $$Q_{AMBIENT} = \int_{\lambda=600\ nm}^{1000} G(\lambda)A(\lambda)\,d\lambda \quad [1]$$

$$Q_{LAMP} = K \int_{\lambda=600\ nm}^{1000} G(\lambda)L(\lambda)\,d\lambda \quad [2]$$

$$K = \frac{\int_{\lambda=600\ nm}^{1000} G(\lambda)A(\lambda)\,d\lambda}{\int_{\lambda=600\ nm}^{1000} G(\lambda)L(\lambda)\,d\lambda}. \quad [3]$$

Q, the integrated night vision goggle-weighted irradiance, is therefore a weighted constant for any specified goggle and irradiance combination. The response of a radiometric-based device such as that disclosed by the present invention can be tailored to detect a level of irradiance present and provide an indication that proper irradiation level is achieved. The measuring device 112 of the present invention contains a radiometric energy detector with accompanying electronic circuitry providing a range of selectable, preset (weighted) Q's, allowing the re-creation of commonly encountered lighting conditions for a given piece of night vision equipment and irradiating lamp spectral distribution.

Figure 4:
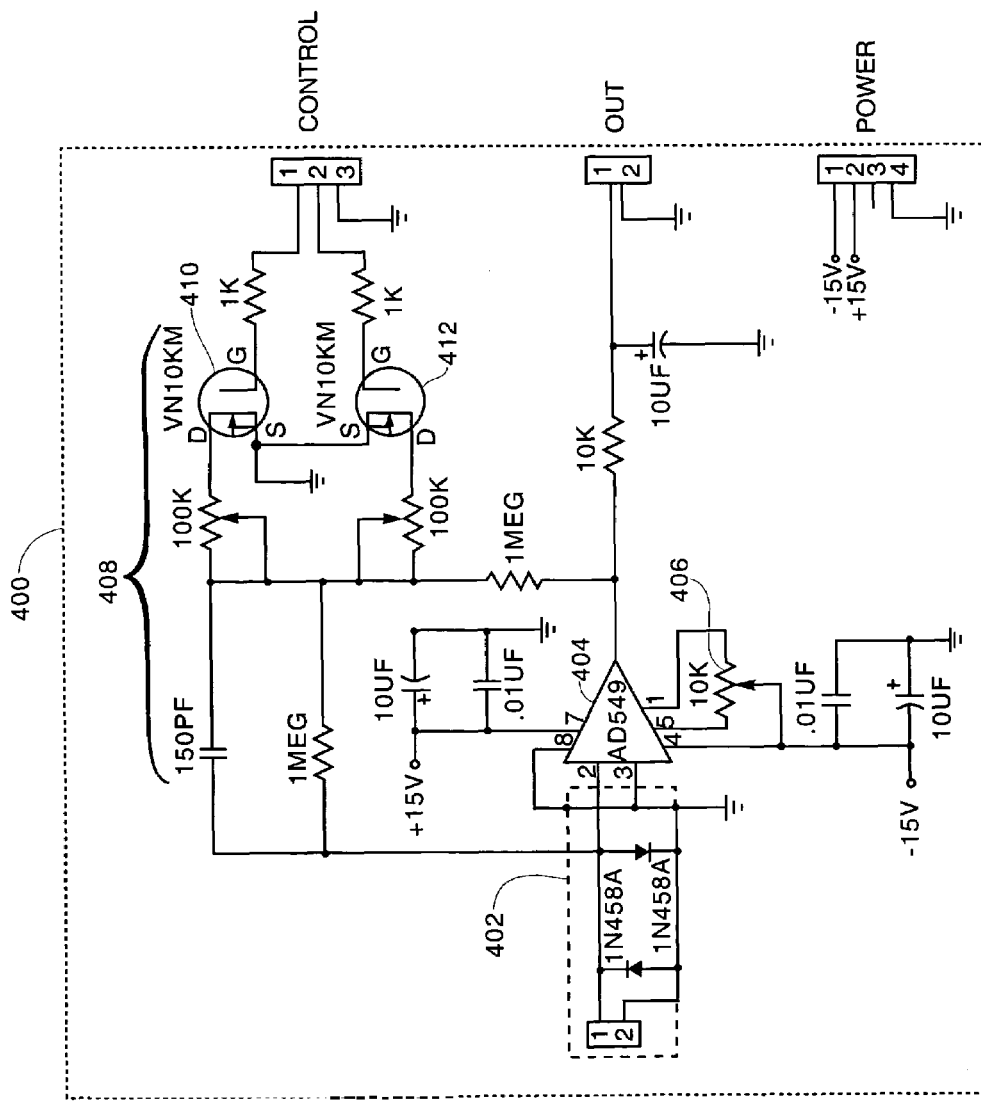
FIG. 4 shows an electrical schematic diagram of a preamplifier circuit used in the FIG. 3 apparatus.

FIG. 4 and FIG. 5 in the drawings show electrical schematic diagrams for a preferred arrangement of apparatus usable for irradiance measurement in the present invention irradiance testing. The FIG. 5 drawing consists of the portions FIG. 5a, FIG. 5b, FIG. 5c, FIG. 5d and FIG. 5e. Thus FIG. 5 shows an overall diagram of the signal processing circuits and electrical signal flow used in the invention and FIG. 4 shows details of one portion of the FIG. 5 apparatus, the photodiode preamplifier appearing at 400 in the FIG. 5 drawing. Significant portions of the signal processing accomplished in the FIG. 5 measurement circuit occur in the form of software embodied into the microprocessor 518 in the FIG. 5 diagram. This software is disclosed in the form of a code listing contained in the compact disc appendix identified above and incorporated by reference herein.

The Silicon photodiode used to generate an electrical signal proportional to the level of irradiance received at the FIG. 1 chart 104 appears at 500 in the FIG. 5 drawing. This photodiode is identified as preferably being of the type PIN IODP devices available from UDT Sensors Incorporated of Hawthorne, Calif. The photodiode is operated in the photoconductive mode of operation by direct coupling to the input terminals of the operational amplifier 404 in the FIG. 4 preamplifier circuit. The operational amplifier 404 is preferably of the low offset voltage type and when provided with the DC offset adjustment of the potentiometer 406 provides a ground referenced output signal from the preamplifier.

The operational amplifier 404 provides a large signal voltage gain by way of the Tee connected feedback network indicated at 408 in FIG. 4. The magnitude of this gain is determined by the activated one of the field effect switching transistors 410 and 412 and the selected resistance of the associated 100 K transistor drain-connected potentiometer. The shielded input network 402 of the operational amplifier 404 includes two oppositely connected diode elements to provide excessive voltage and static electricity protection. Signals in the range of 0 to +10 volts occur at the output of the operational amplifier 404. The needed bipolar supply voltages for the low offset operational amplifier 404 preamplifier are provided by the DC to DC inverter circuit shown at 516 in the FIG. 5a drawing.

Figure 5A:
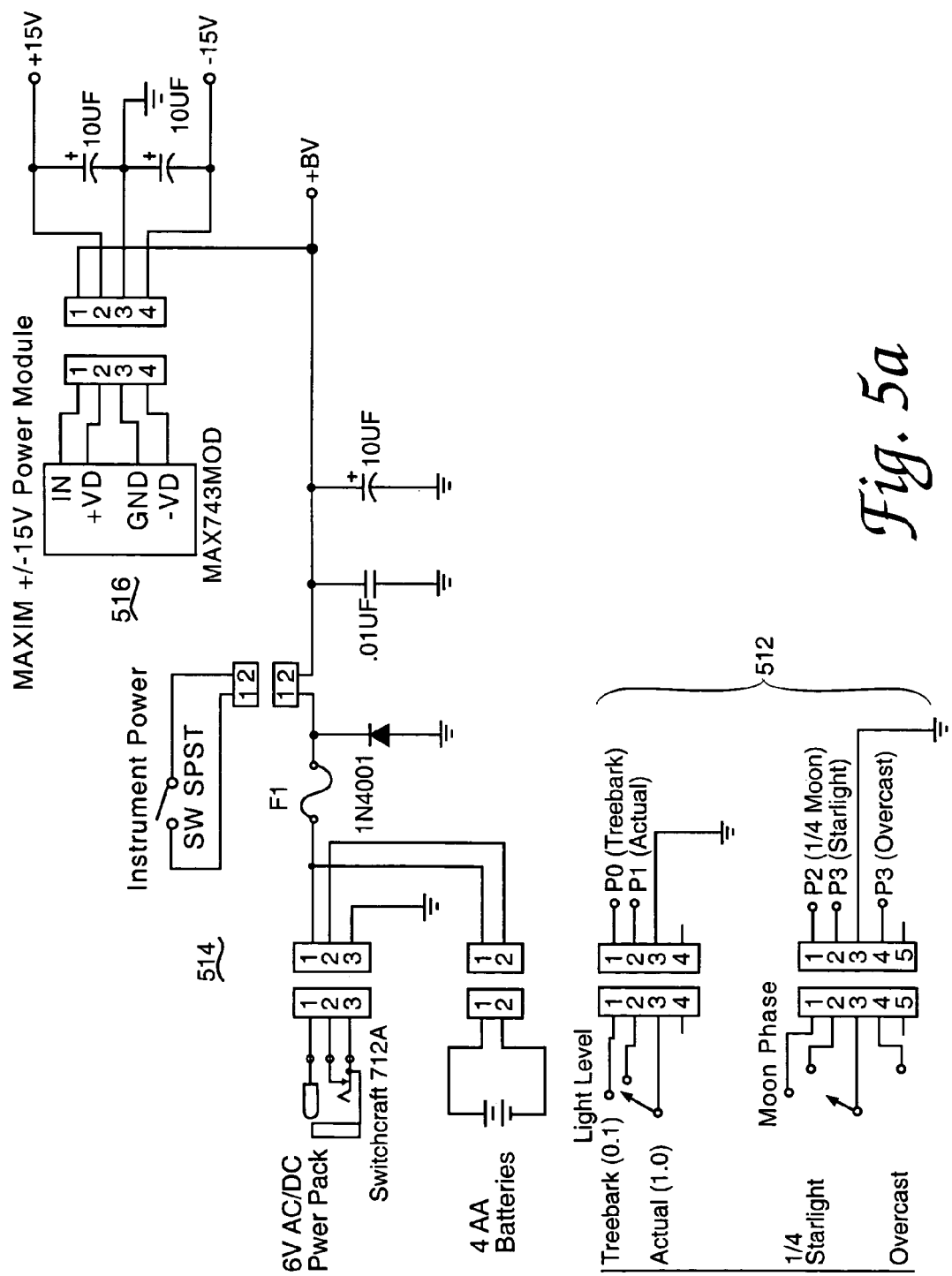
FIG. 5 includes the portions FIG. 5a, FIG. 5b, FIG. 5c, FIG. 5d and FIG. 5e and shows an electrical schematic diagram of a computer inclusive embodiment of the present invention.
Figure 5B:
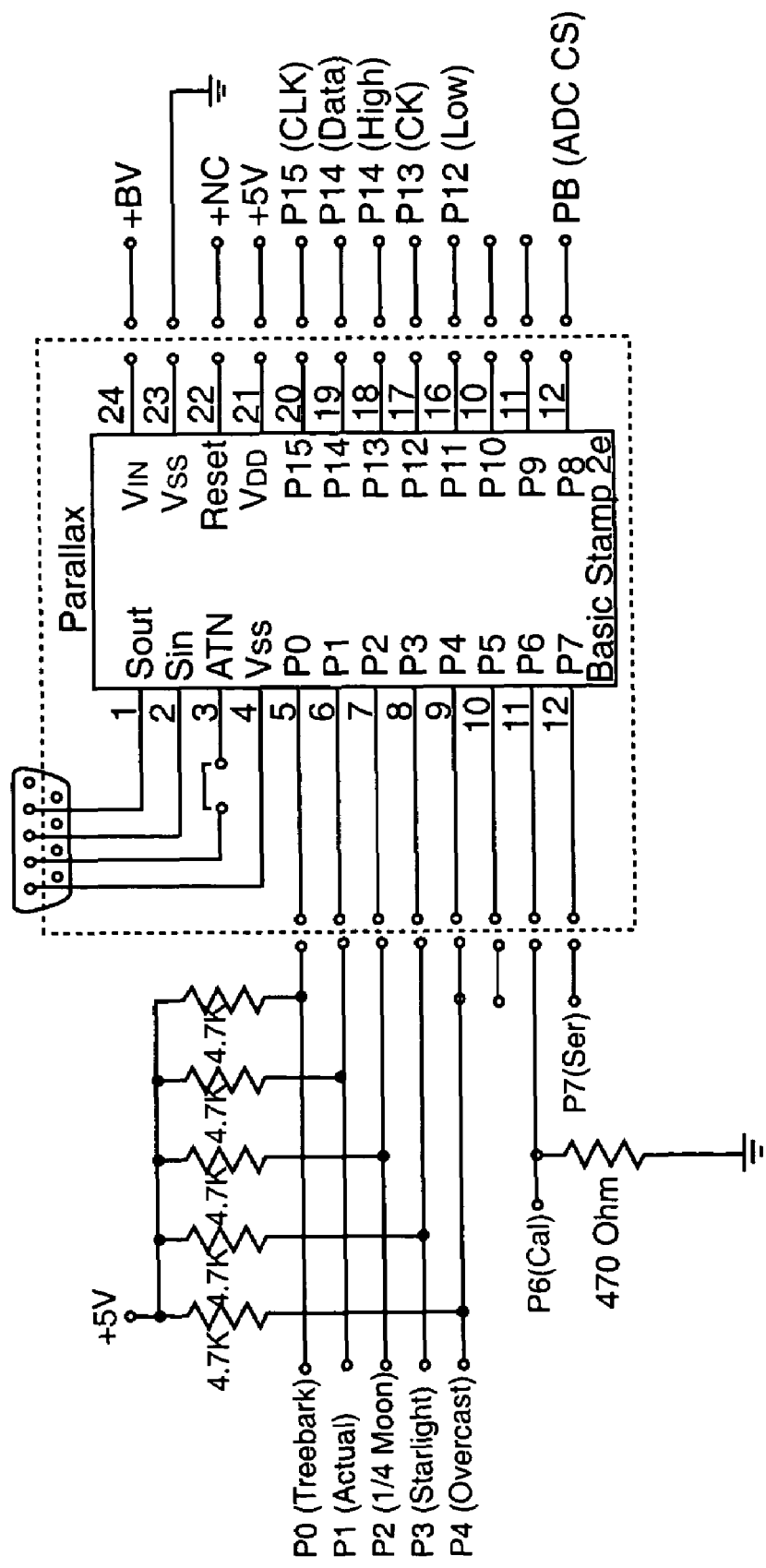
Figure 5C:
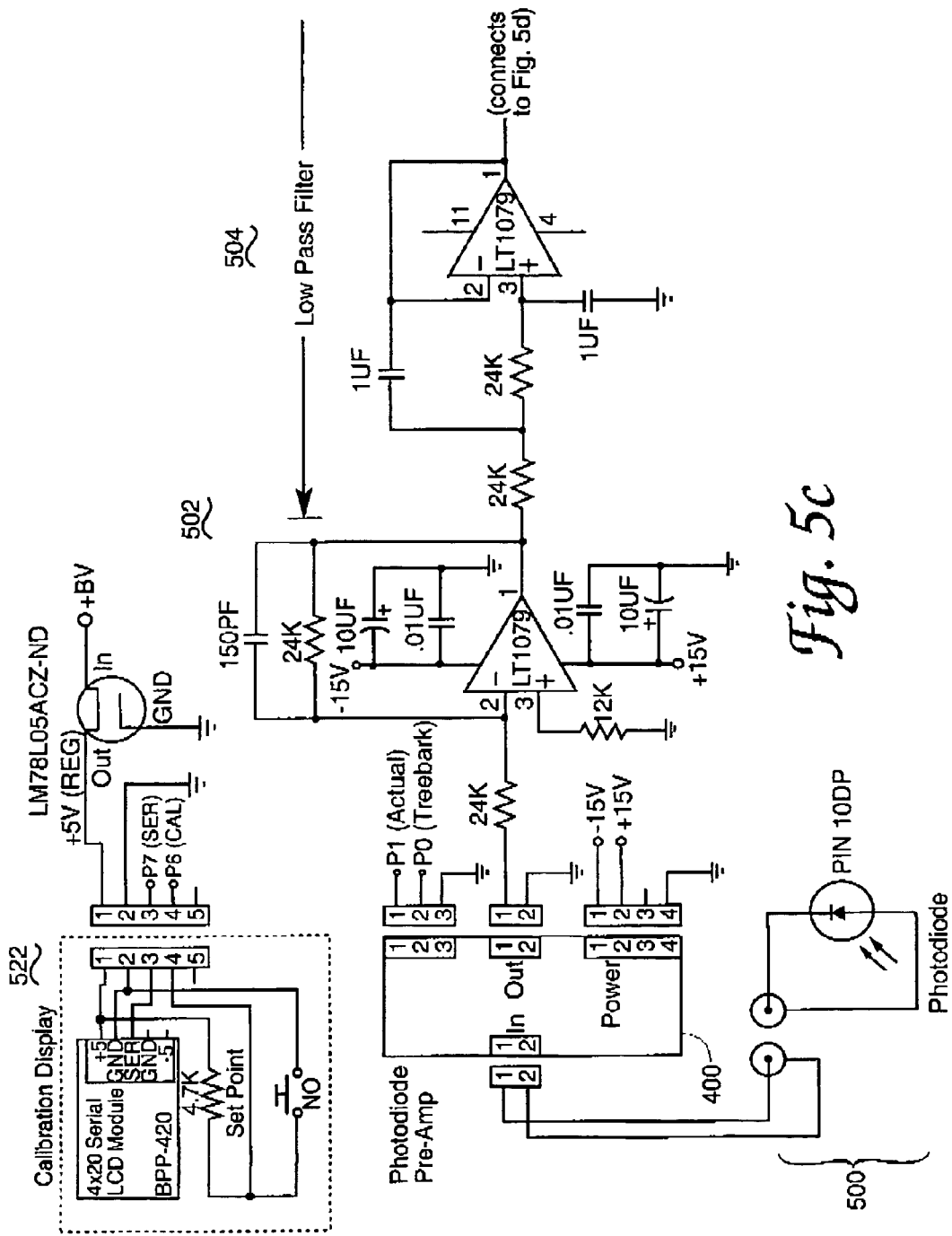
Figure 5D:
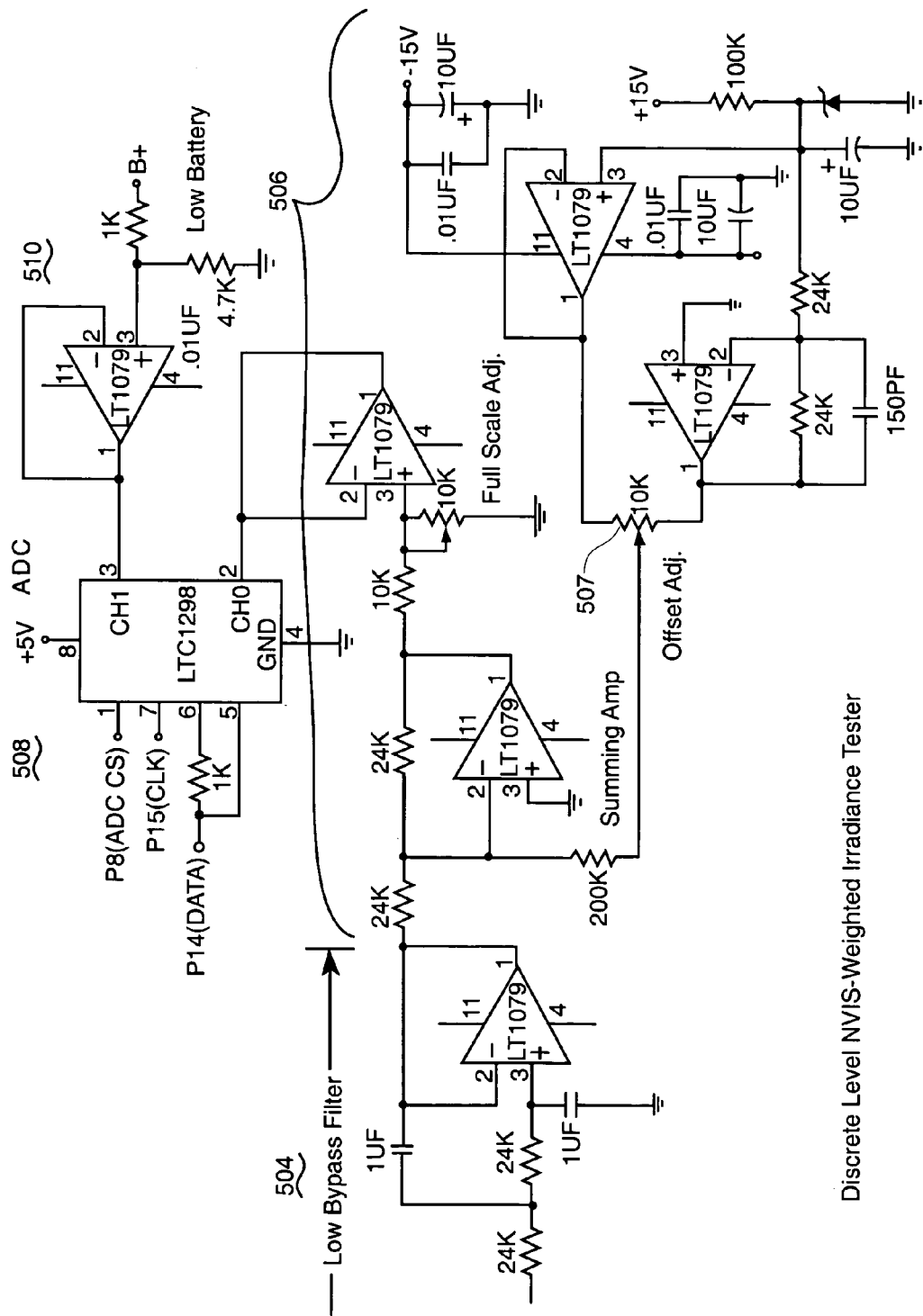
Figure 5E:
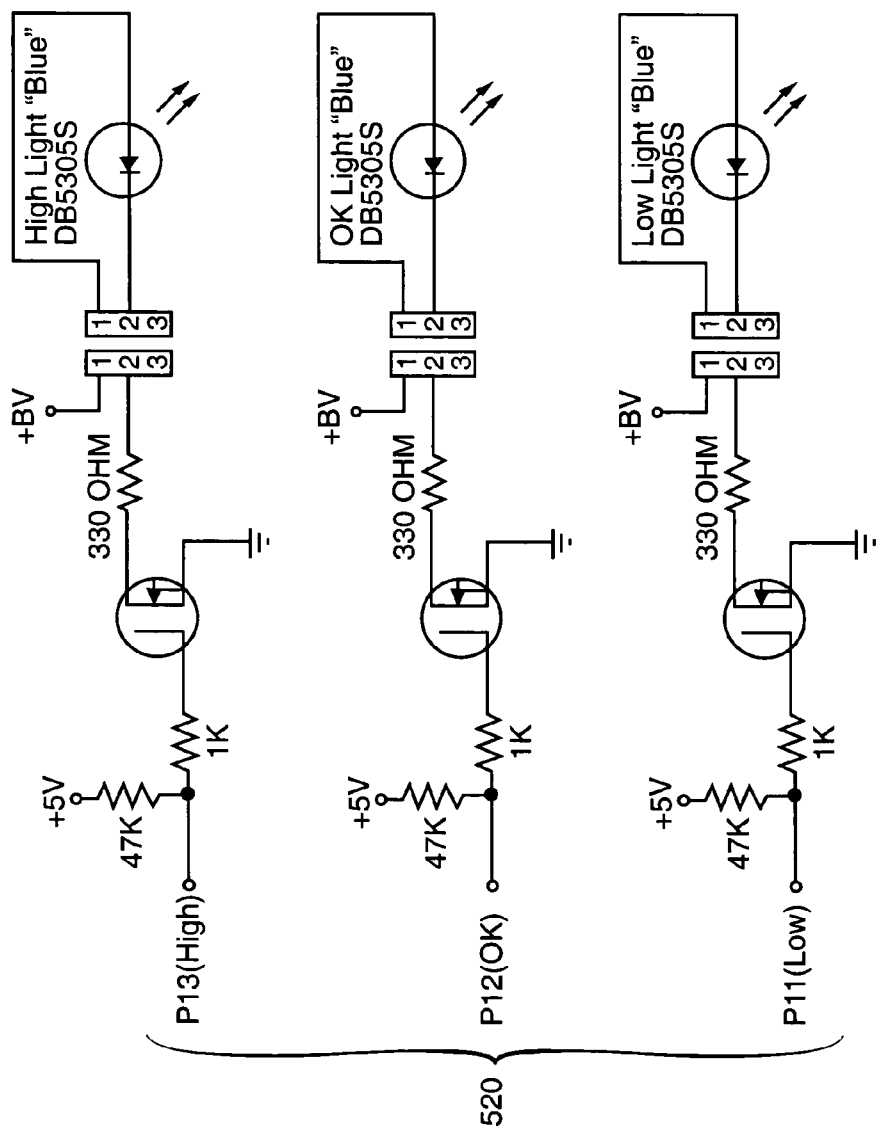

Unity signal gain, buffering and signal inversion are provided by the operational amplifier shown at 502 in the FIG. 5c drawing; this is followed by two stages of low pass waveform filtering provided in the form of active filtering by the operational amplifiers shown at 504 in FIG. 5c and FIG. 5d. Low pass filtering is desirable in the FIG. 5 circuit especially in order to remove components of alternating current ripple possibly existing in the photodiode signal as a result of the FIG. 1 lamp source 110 being energized with alternating current energy. In differing arrangements of the invention, a higher voltage lamp with its resulting small filament and small thermal mass is likely to provide such ripple; a direct current energized lamp source at 110 may generate so little of this ripple as to enable omission of the filter at 504.

The analog-to-digital converter circuit shown at 508 in the FIG. 5d drawing provides digital output signals from the offset and adjusted full-scale analog photodiode signal achieved with the four operational amplifiers at 506 in the FIG. 5d drawing. Digital output signals from the analog-to-dial converter 508 are received into the microprocessor 518 by way of one input port signal path of the micro controller or microprocessor 518. A second input channel on pin 3 of the FIG. 5d analog-to-digital converter 508 provides warning of a low battery or low power supply voltage condition at 514 in FIG. 5a by way of the resistor divider and buffer amplifier at 510 in FIG. 5e and a warning alert light emitting diode driven from the microprocessor 518. The intentional appearance of a strong warning input signal thus discourages further operation of the FIG. 1 apparatus until battery or voltage correction occurs through operator intervention.

In other words, the summing amplifier at 506 in FIG. 5d drawing combines the photodiode low pass filter signal from the filter 504 and an offset adjustment voltage from the potentiometer at 507 for amplifier circuit biasing. The summing amplifier's 0 to +10 volt analog output signal is reduced by the full-scale adjustment amplifier to a 0 to +5 volt range so the signal can be handled by the analog-todigital converter circuit 508. The pin 2 first input channel of the two input channel analog-to-digital converter circuit shown at 508 provides a digital output from the adjusted full-scale analog photodiode signal achieved with the four operational amplifiers at 506. The two input channel analog-to-digital converter circuit shown at 508 communicates with the FIG. 5b microprocessor 518 by way of a single bidirectional port of the microprocessor. The second input channel of the analog-to-digital converter 508 responds to battery and power supply voltage condition at 514 in FIG. 5a by way of a microprocessor 518 driven flashing "too low" detection range blue light emitting diode at 520 in FIG. 5e; this warning also appears physically at 312 in FIG. 3. The appearance of a flashing "too low" detection range blue light emitting diode on the measurement device 112 in FIG. 1 suggests discontinued operation of the apparatus until battery or voltage correction occurs.

Figure 3:
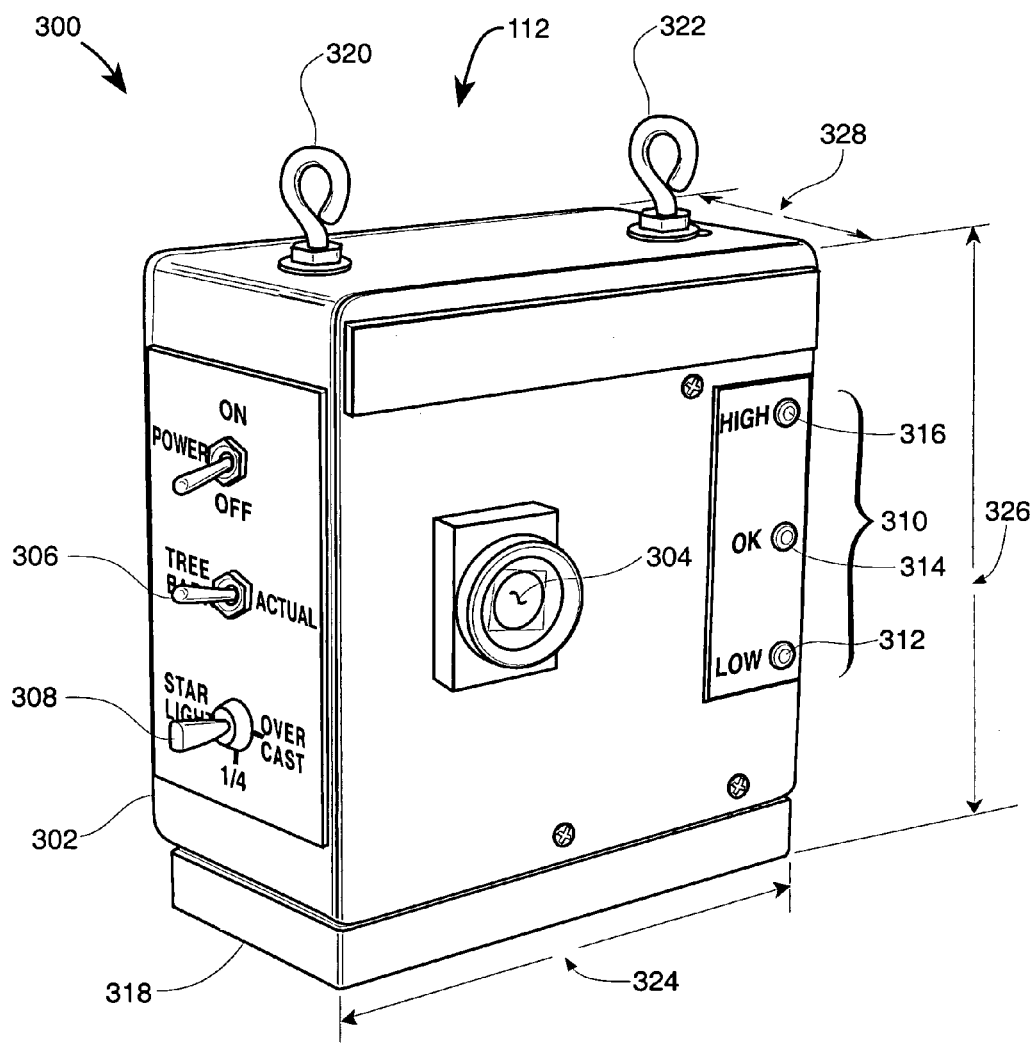
FIG. 3 shows an overall external view of an apparatus made in accordance with the present invention.

The illumination range setting switches used to accommodate the ambient light conditions and viewed object reflectivity variables encountered by a tested night vision device appear as the centermost and lowermost switches 306 and 308 in the FIG. 3 drawing and are represented at 512 in the FIG. 5a drawing. Two switches are used in this function in order to accommodate several night vision apparatus input conditions; either centermost switch 306 setting being usable with either lowermost switch 308 setting. The three position lowermost FIG. 3 switch 308 elects starlight, one-quarter moon and overcast starlight input conditions for the measuring device 112. These settings correspond to night vision goggle-weighted irradiance levels of $5.85 \times 10^{-9}$, $2.08 \times 10^{-8}$ and $5.85 \times 10^{-10}$ watts per centimeter squared (w/cm$^2$) respectively for a Class A night vision goggle. Additional information regarding the illumination levels encountered by night vision apparatus is contained in the military standard MIL-L-85762A the most current version of which is dated 24 Jan. 1986. This standard is also hereby incorporated by reference herein.

In the "actual" setting of the centermost switch 306 in FIG. 3, the measuring device 112 is conditioned for response to the input levels previously noted. In the "tree bark" setting of this switch 306 the expected input levels are one-tenth of these "actual" levels. Tree bark is a low light reflectivity natural material commonly used by convention as a lower limit extremity example in the night vision art and is generally associated with a reflection of about 1/10 of the ambient illumination. The purpose of this setting is to adjust for the fact that the resolution chart 104 in FIG. 1 is typically 90% reflective instead of the 10% reflectivity of tree bark. This produces an apparent night vision goggle radiance of the 90% reflective chart that simulates the radiance level that would be obtained from the 10% reflective tree bark. By way of the lowermost three-position switch 308 and the centermost two position switch 306 the FIG. 3 apparatus is therefore provided with ability to respond to the six input irradiance levels of $5.85 \times 10^{-9}$, $5.85 \times 10^{-10}$, $2.08 \times 10^{-8}$, $2.08 \times 10^{-9}$, $5.85 \times 10^{-10}$, and $5.85 \times 10^{-11}$ watts per centimeter squared (w/cm$^2$).

The switches shown in FIG. 3 and at 512 in FIG. 5 provide direct current zero voltage levels that are applied as logic signals to a plurality of different input port nodes of the microprocessor 518. A reading of these logic signals as well as the analog to digital converter 508 output signals occurs in the software code embedded in the microprocessor 518; these readings for example occur by way of the code titled "GNG" and "CalcMoon" in the microprocessor code appearing in the compact disc appendix associated with this document. The two switches shown in FIG. 3 and at 512 in FIG. 5 select one of six input irradiance levels for the device to measure.

During operation of the FIG. 5 apparatus the output signal of the silicon detector 500 thus is amplified and then fed to the microprocessor 518. The microprocessor 518 also decodes the pre-selected binary switch settings at 512 for determining the expected input irradiance level. The detector's output is compared by the microprocessor to three predetermined weighted constants (Q) representing the desired detection range (high, correct, low) for any received goggle/illumination condition. The microprocessor also activates the appropriate light emitting diodes in the display at 520 in FIG. 5 to indicate the direction (increase/decrease) in which the current light intensity should be adjusted and when the proper illumination level has been achieved. Preferably the display light emitting diodes at 520 are operated in a cumulative manner with the lower two diodes being "ON" indicating a desired chart illumination level and with all three diodes being "ON" indicating an excessive level of illumination. A decision regarding which diodes are to be illuminated commences at the end of the code titled "CalcMoon" in the microprocessor appendix code listing for example. The "ok" value is stored into memory and the "High" and "Low" values are calculated by the microprocessor to determine which light pattern should be displayed.

The microprocessor 518 may be embodied as a "Basic Stamp" type 2e micro controller as is made by Parallax Corporation of Rocklin, Calif., http://www.parallax.com/. Other microprocessors or hardwired logic may be used to achieve the control and memory and other functions accomplished in the Parallax microprocessor with suitable modifications of the software and other microprocessor determined aspects of the invention.

An electrical battery, a power-supply connection jack, a fuse and an ON-OFF switch for the FIG. 5 apparatus also appear at 514 in the FIG. 5a drawing. The power supply connection jack at 514 is preferably made to be of the switching type in order to allow laboratory or other non-portable use of the invention with a power supply and without battery consumption. The diode appearing immediately to the right of the fuse at 514 serves as protection against damaging reverse polarity connection of battery or power supply to the apparatus, current conduction in this diode acts to overload the fuse and open the electrical circuit in crowbar fashion in the event of reverse polarity application. Four alkaline PtAA size batteries serve to operate the 20 milliamp load of the irradiance measuring apparatus for a period of at least sixty hours; Lithium or other high capacity batteries may be substituted for longer operating life. Rechargeable batteries may also be used if desired.

Figure 6:
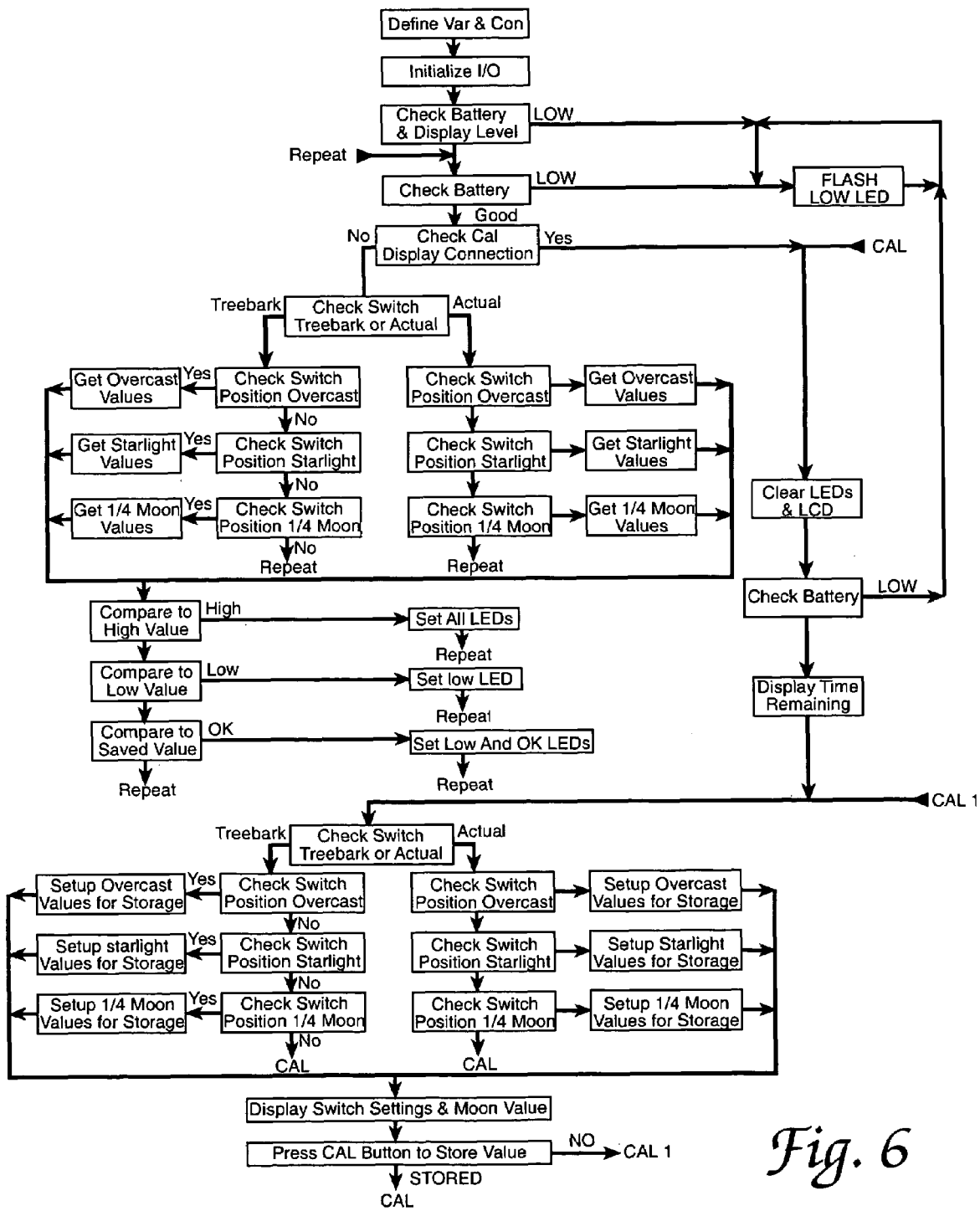
FIG. 6 shows a flow chart relevant to computer software used with the invention, software disclosed in the above identified compact disc appendix of the present document.

The software code disclosed in the compact disc appendix for use in the microprocessor 518 of the FIG. 5 apparatus cooperates with the electrical circuits shown in FIG. 5 to achieve functional operation of the present invention. This code consists of seven different areas as are set off by titles having double lines above and below the title words in the compact disc listing. A flow diagram for the software code appears in abbreviated language form in the several parts of the FIG. 6 drawing herein.

In order to use the present invention an operator may set up a test and adjustment sequence in the manner shown in FIG. 1, place the device's controls in the desired conditions, turn-off the room lights, and then move the light source 110 back and forth to a desired distance with respect to the resolution chart 104, or adjust the light source aperture size, until the device 112 indicates a proper night vision device weighted illumination is falling on the surface of the resolution chart. The finest resolvable square-wave pattern in the resolution chart 104 then indicates the limiting resolution of the night vision device and identifies an achieved equivalent Snellen visual acuity such as 20/50 or 2.5 arc minutes. Normal limiting resolution for any given night vision device type for a specified nighttime ambient illumination is known and a deviation from the norm thus indicates improper adjustment or below acceptable optical performance necessitating appropriate action. The night vision device at 102 in FIG. 1 may of course be of the night vision goggle or night vision telescope or night vision periscope or other night vision device types.

FIG. 3 in the drawings shows an external overall perspective view of a measuring device 112 made in accordance with the invention. As shown in this drawing the measuring device may be contained in a box-like plastic housing 300 and disposed in the FIG. 1 scene by either hanging from the lanyard attachments at 320 and 322 or by mounting via the base plate 318 using a ¼-20 threaded member such as the attachment screw of a photographic tripod or by supporting on one of its flat surfaces. Suitable external dimensions for the preferably unreflective black housing 300 appear at 324, 326 and 328 in the FIG. 3 drawing. Typical numeric values for these dimensions are 4¹¹⁄₁₆ inches, 4¹¹⁄₁₆ inches, and 2⅜ inches respectively. The sensitivity electing switches for the FIG. 8 irradiance measuring apparatus, i.e., the switches at 512 in FIG. 5a, appear at 306 and 308 within the control area face 302 in the FIG. 3 drawing; the power switch at 514 in FIG. 5a appears uppermost in FIG. 3 and is made to move in a plane orthogonal to that of the switches 306 and 308 for darkened room use convenience.

The photodiode at 500 in FIG. 5 receives input irradiance via the aperture shown at 304 in the FIG. 3 view of the measuring apparatus 112. A protective cap cover and mating receptacle may be provided around the photodiode aperture 304 for physical protection purposes. The light emitting diodes of the output display at 520 in FIG. 5 appear at 312, 314 and 316 in FIG. 3. The preferred blue color output of these diodes does not disturb the night vision device under test even though the overall output display 310 is oriented to directly face the night vision device and the lamp 110 in the FIG. 1 typical irradiance-measuring scene. As indicated in connection with the FIG. 5 drawing, energization of the light emitting diodes 312, 314 and 316 is preferably accomplished in cumulative, multiple light emitting diode energized in unison, fashion for "too low", "ok" and "too high" measurements of illumination level by the measuring device 112.

A calibration display for the irradiance measuring device 112 appears electrically at 522 in the FIG. 5c drawing. This display 522 is preferably of the liquid crystal type and is a separate external unit from the measuring device 112 in the FIG. 3 drawing. This calibration display 522 is thus separate and distinct from the blue light emitting diodes circuits at 520 in FIG. 5e drawing. The display 522 is usable for maintenance and adjustment of the correct or center weighted irradiance level constant for each position of the sensitivity switches 306 and 308 in the FIG. 3 drawing. The display unit 522 indicates which sensitivity setting is currently invoked for the measurement system and the incident irradiance level. The normally open switch associated with the display unit 522 provides a means to adjust or recalibrate the center weight irradiance level constant for each position of the sensitivity switches 306 and 308. The transistor device connected to the connector pin 1 of the display 522 is a five-volt regulator providing a stable operating supply voltage for the liquid crystal module used in this display.

From a perspective view of the present invention it is interesting to note that the measuring device 112 is considered to be of a night vision goggle-weighted nature. This wavelength weighting is accounted for in the described apparatus in the calibration procedure in setting of the electronics. Since the described radiometric detector does NOT include a wavelength filter that properly weights the input irradiance it is necessary that it be calibrated with an irradiance source of known NVIS weighted irradiance. The device will then function properly when the irradiating sources used later have the same color temperature as the source that was used to set the calibration values.

While the apparatus and method herein described constitute a preferred embodiment of the invention, it is to be understood that the invention is not limited to this precise form of apparatus or method and that changes may be made therein without departing from the scope of the invention as is defined in the appended claims.

We claim:

1. Portable military field use night vision device evaluation apparatus comprising the combination of:

a standardized military night vision device performance assessment chart including a plurality of night vision device resolution patterns of selected line width and line spacing character;

a source of military night vision device compatible selectable irradiance disposed in proximity with said military night vision device performance assessment chart;

a portable irradiance measuring apparatus disposed within an area irradiated by said source of military night vision device compatible selectable irradiance;

said portable irradiance measuring apparatus including a received irradiance to first electrical signal transducer element, a plurality of selectively accessed standardized ambient irradiance-related reference second electrical signals and an electrical signal comparison apparatus connecting with each said first and second electrical signals; and said electrical signal comparison apparatus including analog to digital converter and signal processing elements coupled to an evaluation apparatus containing a remotely visible, graphic multiple luminous element, military night vision device-indiscernible irradiance level indicating display.

2. The portable military field use night vision device evaluation apparatus of claim 1 wherein said transducer element is a silicon photodiode that is connected to a high gain low offset level direct current preamplifier having a plurality of electrically selectable gain settings and a limited band pass direct current amplifier element connected to a signal output port of said direct current preamplifier.

3. The portable military field use night vision device evaluation apparatus of claim 2 wherein said direct current preamplifier electrically selectable gain settings include tree bark reflectivity, fractional moon phase and overcast starlight irradiance accommodating gain settings.

4. The portable military field use night vision device evaluation apparatus of claim 2 wherein said high gain low offset level direct current preamplifier includes a tee configured resistive gain controlling network and a plurality of resistive element selecting transistor switch elements.

5. The portable military field use night vision device evaluation apparatus of claim 1 wherein said portable irradiance measuring apparatus signal processing elements includes a programmed microprocessor storing said plurality of selectably accessed standardized ambient irradiance related reference second electrical signals and controlling said graphic multiple luminous element military night vision device-indiscernible irradiance level indicating display.

6. The portable military field use night vision device evaluation apparatus of claim 1 wherein said standardized military night vision device performance assessment chart is comprised of at least four differing patterns of selected line width, line spacing and line directional orientation.

7. The portable military field use night vision device evaluation apparatus of claim 1 wherein said source of military night vision device compatible selectable irradiance levels low level illumination includes a source of selected color temperature irradiance illumination and one of an aperture size and a selected source to performance assessment chart distance irradiance level controls.

8. The portable military field use night vision device evaluation apparatus of claim 1 wherein said portable irradiance measuring apparatus includes night vision goggle weighted measuring sensitivities between $2.08 \times 10^{-8}$ and $5.85 \times 10^{-11}$ watts per centimeter squared.

9. The portable military field use night vision device evaluation apparatus of claim 1 wherein said electrical signal comparison apparatus remotely visible graphic multiple luminous element military night vision device-indiscernible irradiance level indicating display includes a plurality of light emitting diode elements having a light output spectrum in a blue wavelength shorter than an input pass band of said military night vision device.

10. The portable military field use night vision device evaluation apparatus of claim 1 wherein said source of military night vision device compatible selectable irradiance levels includes a black body irradiance source operating at a temperature of 2856 degrees Kelvin.

11. The portable military field use night vision device evaluation apparatus of claim 1 wherein said evaluation apparatus containing a remotely visible, graphic multiple luminous element is contained within said portable irradiance measuring apparatus.

12. The pre use method of tuning the performance of a night vision apparatus comprising the steps of:
inputting visual data from a resolution chart of night vision apparatus responsive graded bar patterns into a night vision apparatus being tuned;
irradiating said resolution chart of night vision apparatus graded bar patterns from an irradiance source having output energy within spectral and irradiance level ranges of said night vision apparatus during said inputting step;
selecting a first night scene irradiance of said resolution chart of night vision apparatus graded bar patterns during said inputting step using a first predetermined sensitivity setting of a night vision-irradiance level measuring instrument;
maintaining said selected irradiance of said chart of night vision apparatus resolution graded bar patterns at said first night scene radiance level during a performance adjusting sequence for said night vision apparatus using said first predetermined sensitivity setting of said night vision-irradiance level responsive measuring instrument; and
repeating said inputting, selecting and maintaining steps at a series of additional differing night scene irradiances of said resolution chart, additional irradiances selected and maintained through different predetermined sensitivity settings of said night vision-irradiance level responsive measuring instrument.

13. The pre use method of tuning the performance of a night vision apparatus of claim 12 wherein:
said resolution chart of night vision apparatus responsive graded bar patterns includes a plurality of resolution patterns each having one of differing line width, line spacing and line orientation; and
said step of irradiating said resolution chart of night vision apparatus graded bar patterns from an irradiance source having output energy within spectral and irradiance level ranges of said night vision apparatus during said inputting step includes irradiance from an incandescent lamp operating at a selected color temperature.

14. The pre use method of tuning the performance of a night vision apparatus of claim 12 wherein:
said step of irradiating said resolution chart of night vision apparatus graded bar patterns from an irradiance source having output energy within spectral and irradiance level ranges of said night vision apparatus during said inputting step includes illuminating said resolution chart from an alternating current energized incandescent filament operating at 2856 degrees Kelvin; and
said step of selecting a first night scene irradiance of said resolution chart includes excluding by electrical wave filtering an alternating current signal component of an electrical signal generated within said night vision irradiance level measuring instrument in response to said step of irradiating said resolution chart from an alternating current energized incandescent filament.

15. The pre use method of tuning the performance of a night vision apparatus of claim 12 wherein:
said step of selecting a first night scene irradiance of said resolution chart of night vision apparatus graded bar patterns during said inputting step using a first predetermined sensitivity setting of a night vision irradiance level measuring instrument includes use of a sensitivity setting relating to one of a tree bark reflection, a fractional lunar exposure and a starlight irradiance event.

16. The pre use method of tuning the performance of a night vision apparatus of claim 12 wherein:
within said maintaining step said performance adjusting sequence comprises at least one of a lens focusing adjustment, an angular adjustment and an interpupillary distance adjustment.

17. Portable field deployable computerized military night vision device pre use evaluation apparatus comprising the combination of:
a standardized military night vision device performance assessment chart including a plurality of night vision device resolution patterns of selected line densities and line spacing ranging in pattern frequency content;
a source of military night vision device-compatible 2856 degrees Kelvin operating temperature, selectable irradiance levels low level irradiance disposed in proximity with said military night vision device performance assessment chart;
a digital portable irradiance measuring apparatus disposed within an area irradiated by said source of military night vision device compatible selectable irradiance levels in selected physical proximity with said military standardized night vision device performance assessment chart;
said digital portable irradiance measuring apparatus including a received irradiance to first electrical signal silicon photodiode transducer element, a low offset level direct current preamplifier having a plurality of control signal selectable gain settings, a limited band pass direct current amplifier connected to a signal output port of said direct current preamplifier, an analog to digital converter connected to a signal output port of said limited band pass direct current amplifier and a digital portable irradiance measuring apparatus programmed digital computer connected to a signal output port of said analog to digital converter;

said digital portable irradiance measuring apparatus programmed digital computer including:

a plurality of memory stored selectably accessed standardized ambient irradiance related reference second electrical signals;

program means for comparing said first and second electrical signals;

program means for generating a first output electrical signal when said first electrical signal is smaller than an accessed second electrical signal;

program means for generating a second output electrical signal when said first electrical signal is within a selected percentage range of an accessed second electrical signal;

program means for generating a third output electrical signal when said first electrical signal is greater than said selected percentage range of said accessed second electrical signal;

program means for controlling operation of said digital computer and said night vision device pre use evaluation apparatus; and a remotely visible, graphic, three luminous element, military night vision device indiscernible irradiance level indicating display apparatus cumulatively responsive to said digital computer first, second and third output electrical signals.

18. The portable field deployable military night vision device pre use evaluation apparatus of claim 17 wherein said direct current preamplifier includes a pair of switching transistors received in a resistive Tee operational amplifier gain controlling network and responsive to manual switch setting determined output signals of said portable irradiance measuring apparatus programmed digital computer.

19. The portable field deployable military night vision device pre use evaluation apparatus of claim 17 wherein said standardized military night vision device performance assessment chart and said source of military night vision device-compatible 2856 degrees Kelvin operating temperature selectable irradiance levels are disposed in selected distance separation and said selected distance separation is determined by a desired magnitude of said selectable irradiance level.

20. Night vision device evaluation apparatus comprising the combination of:

a standardized night vision device performance assessment chart including a plurality of night vision device resolution patterns of selected line width and line spacing character;

a source of night vision device compatible irradiation disposed in proximity with said night vision device performance assessment chart;

a irradiance measuring apparatus disposed within an area irradiated by said source of night vision device compatible irradiation adjacent said standardized night vision device performance assessment chart;

said irradiance measuring apparatus including a directly received irradiance to electrical signal broadband transducer element and an irradiance level indicating display.

21. The night vision device evaluation apparatus of claim 20 wherein said irradiance level indicating display includes a remotely visible, graphic, multiple luminous element inclusive, military night vision device-indiscernible display array.

22. The night vision device evaluation apparatus of claim 21 wherein said apparatus further includes an irradiance level tolerance bands determining apparatus connected with said graphic display array.

23. The night vision device evaluation apparatus of claim 20 wherein said irradiance measuring apparatus further includes a plurality of selectively accessed standardized irradiance-related reference electrical signals and an electrical signal comparison apparatus.

24. The night vision device evaluation apparatus of claim 20 wherein said irradiance measuring apparatus directly received irradiance to first electrical signal broadband transducer element includes lens-free coupling with said source of night vision device compatible irradiation.

* * * * *